United States Patent [19]

Cullinan

[11] Patent Number: 4,667,030
[45] Date of Patent: May 19, 1987

[54] HYDRAZIDE SUCCINIMIDE DERIVATIVES OF ANTINEOPLASTIC INDOLE-DIHYDROINDOLE ALKALOIDS

[75] Inventor: George J. Cullinan, Trafalger, Ind.

[73] Assignee: Eli Lilly and Company, Indianapolis, Ind.

[21] Appl. No.: 745,562

[22] Filed: Jun. 17, 1985

[51] Int. Cl.$^4$ .................. C07D 519/04; C07K 15/00
[52] U.S. Cl. .................. 540/478; 530/388; 530/809; 530/828
[58] Field of Search .................. 260/244.4; 514/283; 540/478

[56] References Cited

U.S. PATENT DOCUMENTS

| | | | |
|---|---|---|---|
| 3,387,001 | 6/1968 | Hargrove | 540/478 |
| 3,392,173 | 7/1968 | Hargrove | 540/478 |
| 4,046,722 | 9/1977 | Rowland | 530/362 |
| 4,166,810 | 9/1979 | Cullinan et al. | 540/478 |
| 4,191,688 | 3/1980 | Conrad et al. | 540/478 |
| 4,203,898 | 5/1980 | Cullinan et al. | 540/478 |
| 4,388,305 | 6/1983 | Trouet et al. | 548/478 |
| 4,522,750 | 6/1985 | Ades et al. | 530/397 |

FOREIGN PATENT DOCUMENTS

| | | |
|---|---|---|
| 124502 | 11/1984 | European Pat. Off. . |
| 2090837 | 1/1982 | United Kingdom . |
| 2111055 | 6/1983 | United Kingdom ............... 540/478 |
| 2137210 | 10/1984 | United Kingdom ............... 540/478 |
| 2137202 | 10/1984 | United Kingdom . |

OTHER PUBLICATIONS

Blickenstaff, et al., Chemical Abstracts, vol. 94, 114277s (1981).
FACSS Abstract 183, Root et al., Oct. 6-10, 1975.
Teale et al., *Br. J. Clin. Pharm.*, 4, 169-172 (1977).
Langone et al., *Anal. Biochem.*, 95, 214-221 (1979).
Conrad et al., *J. Med. Chem.*, 22, 391-400 (1979).
Barnett et al., ibid, 21, 88-96 (1978).
Neuss et al., *Tetrahedron Letters*, No. 7, 783-787 (1968).
Johnson et al., *Brit. J. Can.*, 44, 372 (1981)(p. 472-475).
Hargrove (III), *Lloydia*, 27, 340-345 (1964).

*Primary Examiner*—Donald G. Daus
*Assistant Examiner*—Diana G. Rivers
*Attorney, Agent, or Firm*—Robert A. Conrad; Leroy Whitaker

[57] ABSTRACT

An antineoplastic dimeric indole-dihydroindole (vinca) alkaloid carrying a hydrazine succinimide group at C-3, capable of forming conjugates with a diacid at C-4.

9 Claims, No Drawings

HYDRAZIDE SUCCINIMIDE DERIVATIVES OF ANTINEOPLASTIC INDOLE-DIHYDROINDOLE ALKALOIDS

BACKGROUND OF THE INVENTION

The alkaloids obtainable from *Vinca rosea* represent one of the most productive areas of chemistry for drugs adversely affecting the growth of experimental malignancies in mammals. Initially, only some of the alkaloids, obtainable from the leaves of the plant by extraction and purifiable by chromatography, were found to be active. These active antineoplastic alkaloids obtained directly from the leaves of the vinca plant included VLB (Vinblastine, vincaleucoblastine), vincristine (leurocristine), leurosine (vinleurosine), leurosidine (vinrosidine), leuroformine (formylleurosine) and deoxy VLB "A" and "B" (4'-deoxy VLB and 4'-deoxyleurosidine). All are dimeric indole-dihydroindoles. Other less abundant antineoplastic alkaloids have also been found.

Chemical modification of the Vinca alkaloids started slowly for several reasons. In the first place, the molecular structures involved are extremely complex, and chemists were slow to find reactions which modified one specific functional group of the molecule without affecting other groups. Secondly, dimeric alkaloids lacking desirable chemotherapeutic properties had been recovered or produced from *Vinca rosea* extracts, and a determination of their structures had led to the conclusion that these inactive compounds were closely related structurally to, and even isomeric with, one or more of the active alkaloids. Thus, it appeared that small chemical changes in the known alkaloids could have a profound effect on antineoplastic activity.

Because of these restrictions, modification of the indole-dihydroindole alkaloids obtained from *Vinca rosea* has centered around three areas of the molecule C-3, C-4' and C-4. In the first place, one of the more recent, and more successful, modifications of the basic indole-dihydroindole structure has been the preparation of C-3 carboxamide and carbohydrazide derivatives, most of which have turned out to be active anti-tumor agents. [See Cullinan et al., U.S. Pat. No. 4,203,898, Conrad et al., U.S. Pat. No. 4,191,688, Cullinan and Gerzon, U.S. Pat. No. 4,166,810, Conrad et al. *J. Med. Chem.*, 22, 391 (1979), and Barnett et al. ibid, 21 88 (1978)]. One of the amides, 4-desacetyl VLB 3-carboxamide (VDS, vindesine), is currently being marketed in several European countries as an oncolytic agent. Vindesine is effective in treating some vincristine-resistant leukemias in addition to many common neoplasms including germ-cell tumors. Amides of leurosine and leuroformine are disclosed in U.S. Pat. No. 4,191,688.

In another type of modification, reaction of the 3-hydroxy and 3-ester functions of an indole-dihydroindole vinca alkaloid with an isocyanate has produced the corresponding oxazolidinedione derivatives, one of which, the N-chloroethyl derivative—vinzolidine—is currently undergoing a clinical trial in humans. These oxazolidinedione derivatives are disclosed in Miller and Gutowski, U.S. Pat. No. RE 30,560, reissued Mar. 31, 1981. Trouet et al., U.S. Pat. No. 4,388,305 disclose anticancer VLB C-3 peptides in which the peptide group contains 1-6 amino acid residues with a terminal free acid or ester group. These amides formed from one amino acid residue are also disclosed in column 15, lines 1-16, of Cullinan et al. (loc. cit.). Trouet et al also used the hydrazide-azide synthetic procedure of Cullinan et al.

In addition to the VLB, VCR etc. hydrazides from Cullinan et al, (loc cit.) and leurosine hydrazide disclosed in Neuss (et al) *Tetrahedron Letters* 783 (1968) (This article, in Table I, page 785, refers to compound XI as VLB hydrazide, but according to the footnote, the compound is actually an 18'-descarbomethoxy derivative-see also line 2 for the correct name for XI), 4-desacetyl VLB hydrazide derivatives are disclosed in Cullinan and Gerzon, U.S. Pat. No. 4,166,810. The named derivatives include mono $C_{1-3}$ alkyl, $\beta$-hydroxyethyl, ethyl, $\beta$-acetoxyethyl, $C_{2-4}$ alkanoyl, dichloroacetyl, benzoyl, $C_{1-3}$ alkylcarbazyl, dimethyl and $C_{1-3}$ alkylidine (=CRR' where R and $R^1$ are H or methyl or one is ethyl).

Imide derivatives of vinca hydrazides are not known.

SUMMARY OF THE INVENTION

This invention provided compounds of the formula

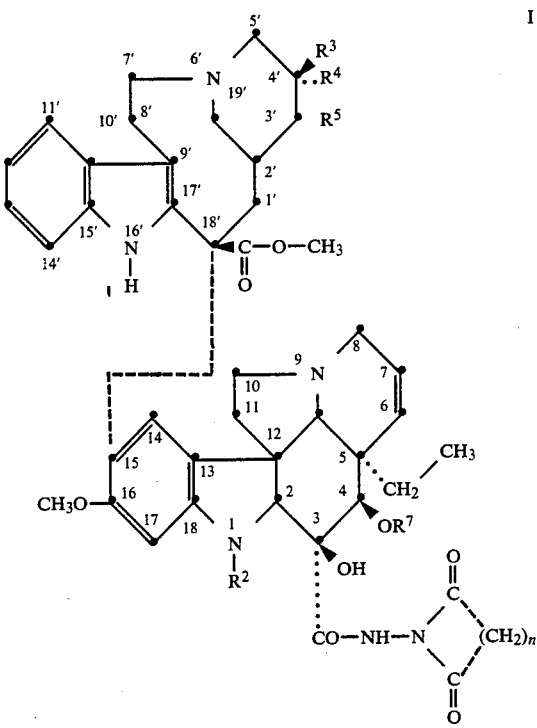

wherein n is 2–4, $R^2$ is $CH_3$ or CHO; when taken singly, $R^5$ is H and one of $R^3$ and $R^4$ is H or OH and the other is $C_2H_5$; when taken together, $R^4$ and $R^5$ form an oxirane ring and $R^3$ is ethyl; $R^7$ is H, $C_{1-3}$alkanoyl, chloro-substituted $C_{1-3}$-alkanoyl, or $CO—X—COR^8$ where X is $C_{2-4}$ alkylene and $R^8$ is OH, $OC_{1-3}$ alkyl or Z, an acylating moiety; and pharmaceutically-acceptable acid addition salts thereof formed with relatively non-toxic acids.

(Compounds according to I are named as $N^2$-succinimide, adipimide or glutarimide derivatives of the basic indole-dihydroindole 3-carbohydrazide (II below), the $N^2$ referring to the fact that the second (beta) nitrogen atom of the hydrazine is part of a cyclic imide ring).

In the above formula, the terms $C_{1-3}$ alkyl-CO and chloro-substituted $C_{1-3}$ alkyl-CO include acetyl, propionyl, chloroacetyl, n-butyryl, isobutyryl, $\alpha$-chloro-n-butyryl, $\alpha$-chloropropionyl and $\alpha$-chloroisobutyryl.

Groups represented by $R^7$ when it is CO—X—$COR^8$, X is $C_{2-4}$ alkylene and $R^8$ is OH include succinoyl [CO(CH$_2$)$_2$COOH], glutaroyl [CO-(CH$_2$)$_3$COOH], adipoyl [CO(CH$_2$)$_4$COOH], 2-methyl adipoyl [CO—CH$_2$—CHCH$_3$—CH$_2$—COOH] and the like. Lower alkyl esters of these acids ($R^8$ is O—$C_{1-3}$ alkyl) would include, for example, the methyl succinate ester [CO(CH$_2$)$_2$COOCH$_3$] and the like.

When $R^8$ is Z, the acylating moiety can be Cl, Br, N$_3$, O—CO—$C_{1-6}$alkyl, imidazolyl,

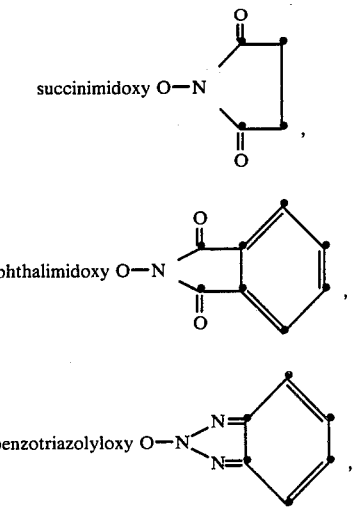

and the like.

In formula I above, where $R^7$ is H, $R^2$ is methyl, $R^3$ is hydroxyl, $R^4$ is ethyl, and $R^5$ is H, 4-desacetyl VLB (4-desacetyl vinblastine) is represented; where $R^7$ is H, $R^2$ is formyl, $R^3$ is hydroxyl, $R^4$ is ethyl and $R^5$ is H, 4-desacetyl vincristine is represented; where $R^7$ is H, $R^2$ is methyl, $R^3$ is ethyl, $R^4$ is hydroxyl, and $R^5$ is H, 4-desacetyl leurosidine is represented; where $R^7$ is H, $R^2$ is methyl or formyl, $R^3$ is ethyl and $R^4$ and $R^5$ taken together with the carbons to which they are attached form an alpha-epoxide ring, 4-desacetyl leurosine and 4-desacetyl leuroformine, respectively are represented; where $R^7$ is H, $R^2$ is methyl, $R^3$ is ethyl, $R^4$ and $R^5$ are H, 4-desacetyl deoxy VLB "B" or 4-desacetyl-4'-deoxyleurosidine or 4-desacetyl-4'-epideoxy 1-formyl-1-desmethyl-4'-deoxyleurosidine) is VLB is represented; where $R^7$ is CO—CH$_3$, $R^2$ is methyl, $R^4$ is ethyl and $R^3$ and $R^5$ are H, —4'-deoxy VLB is represented; where $R^7$ is COCH$_3$, $R^2$ is CHO, $R^3$ is ethyl, $R^4$ and $R^5$ are H, 4-desacetyl-4'epideoxyvincristine (4-desacetyl-represented; and where $R^7$ is COCH$_3$, $R^2$ is methyl, $R^3$ is OH, $R^4$ is ethyl and $R^5$ is H, VLB is represented; etc.

Pharmaceutically-acceptable acid addition salts of the compounds of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxyalkanoic and hydroxyalkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, $\beta$-hydroxybutyrate, glycollate, malate, naphthalene-1-sulfonate, naphthalene-2-sulfonate, mesylate and the like salts.

The compounds of this invention are prepared by reacting a 3-carboxyhydrazide of a 4-desacetyl antineoplastic vinca dimeric indole-dihydroindole alkaloid of structure II

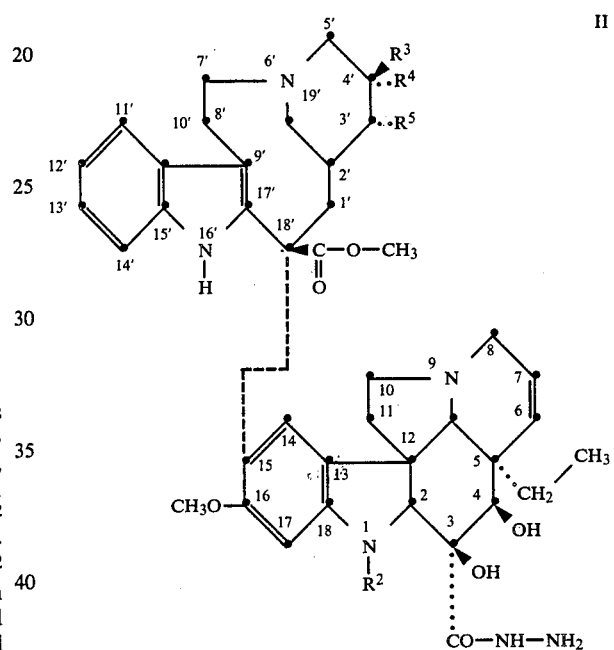

wherein $R^2$–$R^5$ have their previous significance, with succinic, glutaric or adipic anhydride to form a compound of the structure

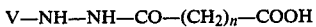

where V represents the vinca alkaloid moiety (all of II except the group attached to the C-3 carbonyl) and n is 2–4.

The terminal free acid group is then converted to a small acylating moiety Z'; i.e., acid chloride, or bromide or mixed anhydride with alkylsulfonic, benzenesulfonic or toluenesulfonic acids or with acetic or propionic acid and the like. The acylating function then spontaneously cyclizes to yield the imides of formula I. This procedure is illustrated below, again using "V" to represent the vinca dimer and the acid chloride as representative of the small acylating group, E'.

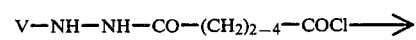

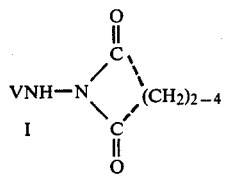

Intermediate according to III and IV above are disclosed and claimed in my co-pending application Ser. No. 745,563, filed June 17, 1985.

The production of a vinca hydrazide invariably is accompanied by hydrolysis of the 4-acetoxy group present in all such starting vinca indole-dihydroindole dimeric alkaloids. The product is a 4-hydroxy derivative. The 4-hydroxy cannot, at this point, be reacylated by the method of Hargrove, U.S. Pat. No. 3,387,001—see also Hargrove, Lloydia, 27 340 (1964)—since the terminal amine group (beta $NH_2$) of the hydrazide will acylate preferentially. Thus, the provision of those compounds according to I above in which $R^7$ is other than H must be carried out by acylating a compound according to I where $R^7$ is H; i.e., a compound in which the succinimide moiety is in place thereby "blocking" the hydrazine beta $NH_2$. However, once the succinimide group is in place, the resulting 4-OH vinca can be acylated by the procedure of Hargrove including the step of removing any 3-acyloxy group by treatment with wet silica gel. Hargrove (loc.cit.) provides directions for the preparation of the analogous 4-acetyl, chloroacetyl etc. derivatives—see also my copending application Ser. No. 593,442 filed 3-26-84, now U.S. Pat. No. 4,596,676 (a copy of U.K. application No. 2,137,202A is provided).

The above synthetic procedures are more specifically exemplified in the following examples.

EXAMPLE 1

Preparation of 4'-Deoxy-4-desacetylleurosidine 3-carboxhydrazide $N^2$-Succinimide A solution was prepared from 1320 mg of 4'-deoxy-4-desacetylleurosidine 3-carboxhydrazide in 25 ml of pyridine. 175 mg of succinic anhydride were added and the reaction stirred at room temperature under nitrogen for about 24 hours. The volatile constituents were then removed from the reaction mixture in vacuo and the resulting residue taken up in methylene dichloride plus sufficient methanol to solubilize the entire residue. The organic layer was twice washed with an equal volume of water and was then dried. Evaporation of the volatile constituents in vacuo gave a residue comprising $N^2$-succinoyl 4'-deoxy-4-desacetylleurosidine 3-carboxhydrazide was dissolved in 25 ml of pyridine to which 350 mg of acetic anhydride were added, thus forming a mixed anhydride of the succinic and acetic acids, which anhydride spontaneously cyclized to yield 4'-deoxy-4-desacetylleurosidine 3-carboxhydrazide $N^2$-succinimide. The reaction mixture was evaporated to dryness in vacuo and the residue was dissolved in methylene dichloride. The methylene dichloride extract was washed twice with an equal volume of water and then dried. Evaporation of the methylene dichloride yielded 4'-deoxy-4-desacetylleurosidine 3-carboxhydrazide $N^2$-succinimide which was chromatographed over silica using ethyl acetate containing increasing amounts (0-50%) of methanol as the eluant. Fractions shown by TLC to contain the desired succinimide derivative were combined and the solid evaporated therefrom in vacuo.

190 mg of 4'-deoxy-4-desacetylleurosidine 3-carboxhydrazide $N^2$-succinimide were obtained having the following physical characteristics:

Infrared spectrum (in chloroform): peaks at 3470, 1736, 1615, and 1572 cm.$^{-1}$.

NMR (CDCl$_3$) : δ at 10.90, 7.88, 7.49, 7.12, 6.48, 6.05, 5.80, 4.10, 3.76, 3.56, 2.82, 0.93, 0.85.

The sulfate salt was prepared by dissolving the free base in anhydrous ethanol at pH=~8.0. The pH was then adjusted to about 3.9 with a freshly prepared solution of 2% ethanolic sulfuric acid. Evaporation of the reaction mixture to dryness yielded 4'-deoxy-4-desacetylleurosidine 3-carboxhydrazide $N^2$-succinimide sulfate.

Following the above procedure, 4-desacetyl VLB hydrazide (2.4 g) was dissolved in 125 ml of pyridine to which 385 mg of glutaric anhydride were added. $N^2$-glutaroyl 4-desacetyl VLB 3-carboxhydrazide thus formed was isolated by the above procedure and purified by chromatography over silica gel using the same solvent system as above. The glutaroyl compound was reacted with acetic anhydride to form the mixed anhydride which cyclized spontaneously to yield 4-desacetyl VLB 3-carboxhydrazide $N^2$-glutarimide. The compound was purified by chromatography over silica gel using the above solvent system. A yield of 460 mg of the $N^2$-glutarimide derivative were obtained having the following physical characteristics: Mass spectrum m/e=864 ($C_{48}H_{60}N_6O_9$). Infrared spectrum (CHCl$_3$): peaks at 3475, 1714, and 1616 cm$^{-1}$.

pKa (66% aqueous DMF)=5.1, 7.4, 12.9.

NMR (CDCl$_3$): δ at 9.96, 8.91, 8.04, 7.52, 7.14, 6.58, 6.08, 5.83, 4.15, 3.78, 3.69, 3.61, 2.86, 0.93, 0.89.

The sulfate salt was prepared by the above procedure; yield=210 mg from 290 mg of starting material.

Following the above procedure but again substituting 4-desacetyl VLB 3-carboxhydrazide for 4'-deoxy-4-desacetylleurosidine 3-carboxhydrazide, and using acetyl chloride in place of acetic anhydride, there was prepared $N^2$-succinoyl 4-desacetyl VLB 3-carboxhydrazide. Chromatography of the succinimide product yielded two fractions, one of which was the expected 4-desacetyl VLB 3-carboxhydrazide $N^2$-succinimide and the other the 4-acetyl derivative thereof which formed as a by-product during the cyclization procedure. 4-Desacetyl VLB 3-carboxhydrazide $N^2$-succinimide had the following physical characteristics. Mass spectrum m/e=850 ($C_{47}H_{50}N_6O_9$).

Infrared spectrum (KBr): peaks at 3480, 1734 and 1616 cm$^{-1}$.

NMR (CDCl$_3$): δ at 9.69, 9.47, 8.22, 7.49, 7.12, 6.53, 6.07, 5.82, 5.71, 4.01, 3.77, 3.63, 3.59, 2.84, 2.82, and 0.89.

The sulfate salt was prepared according to the above procedure; yield=250 mg from 350 mg starting material.

EXAMPLE 2

Preparation of VLB 3-Carboxhydrazide $N^2$-succinimide

A solution was prepared by dissolving 970 mg of $N^2$-succinoyl 4-desacetyl VLB 3-carboxhydrazide from the above example in 25 ml of pyridine. 95 mg of acetyl chloride were added (a 10 molar excess). After a short period of time, another 100 mg of acetyl chloride were added. The volatile constituents were removed in vacuo and the residue dissolved in chloroform plus a small amount of methanol. The organic layer was washed with water and dried. Evaporation of the solvent yielded a residue which was dissolved in methylene dichloride and the methylene dichloride solution, chromatographed over silica gel using the solvent system from Example 1. Fast moving fractions were collected and combined. Evaporation of solvent therefrom yielded 110 mg of VLB 3-carboxhydrazide $N^2$-succinimide having the following physical characteristics Mass spectrum m/e=892 ($C_{49}H_{60}N_{10}$). Infrared speotrum $CHCl_3$): peaks at 3480, 3400, 3020, 1738 and 1616cmhu −1.

Mass spectrum ($CDCl_3$) peaks at 10.3, 8.79, 8.05, 7.54, 7.12, 6.61, 6.08, 5.86, 5.48, 5.33, 3.79, 3.66, 3.61, 2.82, 2.21, 0.89, 0.82.

The sulfate salt was prepared according to the above procedure at pH=about 4.2.

EXAMPLE 3

Preparation of 4-Propionyl VLB 3-carboxhydrazide $N^2$-succinimide

A solution was prepared by dissolving 360 mg of 4-desacetyl VLB 3-carboxhydrazide $N^2$-succinimide from Example 1 in 10 ml of pyridine and 10 ml of methylene dichloride. About 50 mg of propionyl chloride in 1 ml of methylene dichloride were added, and the reaction mixture stirred overnight at ambient temperature. After stirring for about 24 hours, an additional (about) 50 mg of propionyl chloride were added, followed 4 hours later by an additional 100 mg of propionyl chloride. After about 24 hours, the reaction mixture was evaporated to dryness in vacuo and the residue dissolved in methylene dichloride. The methylene dichloride solution was washed twice with equal volumes of water and then dried. Evaporation of volatile constituents in vacuo yielded a residue, TLC of which indicated unreacted starting material. The above preparation was therefore repeated by dissolving the residue in 10 ml of methylene dichloride and 5 ml of pyridine. 100 mg of propionyl chloride were added under nitrogen and the reaction mixture stirred for an additional 24 hours. After about 24 hours, the reaction mixture was evaporated to dryness in vacuo, the residue dissolved in methylene dichloride, and the methylene dichloride solution washed with water. The methylene dichloride solution was dried and the solvent evaporated therefrom in vacuo. Chromatography over silica gel of a methylene dichloride solution of residue using the same solvent system as prewiously, yielded 90 mg of a faster moving spot having the following physical characteristics. Mass spectrum: m/e=906 ($C_{50}H_{62}N_6O_{10}$)

NMR ($CDCl_3$): δ at 8.81, 8.07, 7.51, 7.14, 6.66, 6.08, 5.85, 5.47, 5.30, 3.80, 3.68, 3.64, 2.82, 1.13, 0.92, 0.82.

The sulfate salt was prepared as before; yield=24 mg from 60 mg starting material.

EXAMPLE 4

Preparation of 4-Succinoyl VLB 3-carboxhydrazide $N^2$-succinimide

A solution was prepared by dissolving 1.61 g of 4-desacetyl VLB 3-carboxhydrazide $N^2$-succinimide (from Example 3) in 50 ml of pyridine. 390 mg of succinic anhydride were added and the reaction vessel sealed under $N_2$. After being kept for 5 days at room temperature, the reaction vessel was opened and the contents evaporated to dryness. The resulting residue was dissolved in $CH_2Cl_2$ containing some methanol. The organic layer was washed twice with equal volumes of water and then dried. TLC indicated the presence of starting material; so the dried organic layer was evaporated to dryness and the residue dissolved in 50 ml of pyridine. 400 mg of succinic anhydride were added and the reaction vessel sealed under $N_2$ as before. After remaining for 1 day at room temperature, the vessel was opened and the reaction mixture purified as before except that one wash of the organic layer was with brine. This time, TLC indicated a virtual absence of a spot corresponding to starting material. The residue from evaporating the dried organic layer was therefore chromatographed over $SiO_2$ using ethyl acetate containing increasing amounts of methanol (0 to 50%) as the eluant. Fractions containing 4-succinoyl VLB 3-carboxhydrazide $N^2$-succinimide were combined to yield 570 mg of a compound having the following characteristics:

Infrared spectrum ($CHCl_3$): peaks at 1616 and 1735 $cm^{-1}$.

pKa (66% DMF)=3.9, 7.4 and 13.1.

NMR ($CDCl_3$) δ 8.92, 8.20, 7.50, 7.13, 6.42, ∼6.0, 5.79, 5.49, 5.30, 3.76, 3.64, 3.62, 2.84, 2.81, 0.92, 0.74.

The following illustrates the scope of the compounds represented by I above. In naming these compounds, where a group present in the original indoledihydroindole dimer has been replaced by a new function; i.e., 3-dcarbomethoxy replaced by 3-carboxhydrazide, the group removed will be omitted.

4-desacetyl-4'-deoxy VLB 3-carboxhydrazide $N^2$-adipimide 4-desacetyl-4'-deoxyleurosidine 3-carboxyhydrazide $N^2$-glutarimide 4-desacetyl-4'-deoxy-1-formylleurosidine 3-carboxhydrazide $N^2$-succinimide 4-chloroacetylleurosidine 3-carboxhydrazide $N^2$-succinimide 4-Succinoyl vincristine 3-carboxhydrazide $N^2$-succinimide and the like.

The compounds of this invention have utility as antineoplastic compounds active against transplanted tumors in mice. They also have mitotic activity. As evidence of such utility, the cytostatic activity of the compounds was measured by standard procedures against CCRF-CEM, a human acute lymphoblastic leukemia cell line. Table I gives the results of this study. In the table, column 1 gives the name of the compound, and column 2 the 50% minimum inhibitory concentration of the drug from column 1 in mcg./ml.

TABLE I

| CCRF-CEM CYTOTOXICITY SCREEN | |
|---|---|
| Name of Compound | $IC_{50}$ mcg/ml. |
| 4-Desacetyl VLB 3-carboxhydrazide $N^2$—succinimide sulfate | 0.02 |
| VLB 3-carboxhydrazide $N^2$—succinimide sulfate | 0.01 |
| 4-Propionyl VLB 3-carboxhydrazide $N^2$—succinimide sulfate | 0.01 |
| 4-desacetyl-4'-Deoxyleurosidine 3-carboxhydrazide $N^2$—succinimide sulfate | 0.075 |
| 4-Succinoyl VLB 3-carboxhydrazide $N^2$—succinimide | 0.5 |

Two compounds of this invention, 4-desacetyl VLB 3-carboxhydrazide $N^2$-succinimide and the corresponding glutarimide have demonstrated outstanding activity against the following transplanted tumors in mice: 6C3HED lymphosarcoma, B-16 Sub.C. melanoma, C-26 colon carcinoma, and X-5563 plasma cell myeloma. These results follow.

| In Vivo Test Data | |
|---|---|
| | % INHIBITION |
| VLB C-3-Carboxhydrazide | |
| $N^2$—Succinimide Sulfate | |
| 6C3HED LYMPHOSARCOMA | |
| Dose I.V. × 1 | |
| 4 mg/kg | Toxic |
| 2 | Toxic |
| 1 | 100 |
| 0.5 | 100 |
| 0.25 | 100 |
| 0.125 | 94 |
| 0.0625 | 11 |
| B-16 Sub. C. Melanoma | |
| Dose I.V. 1 & 7 | |
| 4 | Toxic |
| 2 | 91 (1/10) |
| 1 | 82 |
| 0.5 | 51 |
| 25 | 8 |
| C-26 Colon Carcinoma | |
| Dose I.V. 1 & 7 | |
| 4 | Toxic |
| 2 | 73 |
| 1 | 50 |
| 0.5 | 0 |
| 0.25 | 0 |
| X5563 Plasma Cell Myeloma | |
| Dose I.V. 1 & 7 | |
| 4 | Toxic |
| 2 | 94 |
| 1 | 59 |
| 0.5 | 30 |
| 0.25 | 25 |
| 4-Desacetyl VLB Hydrazide | |
| $N^2$—Glutarimide Sulfate | |
| 6C3HED | |
| Dose I.V. × 1 | |
| 8 | Toxic |
| 4 | Toxic |
| 2 | Toxic |
| 1 | 100 (1/10) |
| 0.5 | 100 |
| 0.25 | 100 |
| 0.125 | 80 |
| 0.0625 | 79 |
| 4-Propionyl VLB 3-Carbox- | |
| hydrazide $N^2$—succinimide | |
| sulfate | |
| 6C3HED Lymphosarcoma | |
| Dose I.V. × 1 | |
| 5 mg/kg | Toxic |
| 2.5 | 100 |
| 1.25 | 100 |
| 4-Desacetyl VLB 3-Carbox- | |
| hydrazide $N^2$—succinimide | |
| sulfate | |
| 6C3HED Lymphosarcoma | |
| Dose I.V. × 1 | |
| 5 mg/kg | Toxic |
| 2.5 | 100 |
| 1.25 | 100 |

Compounds according to I above in which $R^7$ is CO—X—$COR^8$, $R^8$ is OH and X is $C_{1-3}$ alkylene not only have antineoplastic activity, but are also useful intermediates for the preparations of novel conjugates comprising a vinca alkaloid moiety hydrolysably linked at C-4 via a group of the formula O—CO—X—CO-immunoglobulin (Ig) or an immunoglobulin fragment (Ig'). The novel conjugate thus prepared is a derivative of a vinca alkaloid, such as for example, a 3-carboxyhydrazide $N^2$-succinimide, adipimide or glutarimide of a neoplastic dimeric indole-dihydroindole alkaloid, (VLB, deoxy VLB "B" etc.) according to I and can have one or more (1–20) such vinca alkaloid moieties covalently attached to each immunoglobulin molecule via amide bonds.

The novel conjugates thus produced are useful, inter alia, in the treatment of cancers. They are potentially more effective and have fewer side effects by virtue, of their ability to increase the concentration of the cytotoxic drug at the site of the tumor. The linkage of the drug moiety via the C-4 "spacer" group VY-COXCO- where V is the vinca moiety frequently enables a greater drug concentration to be formed on the immunoglobulin, thus increasing the efficacy of the conjugate. The invention also includes conjugates for use in an indirect system in which they are employed to recognise an antibody specific to the cell surface antigen.

More particularly, the conjugates of the invention can be represented by the following formula

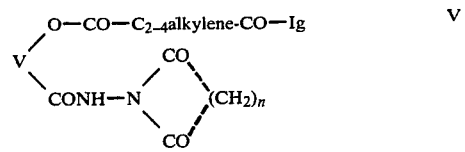

in which n is 2–4, Ig represents an immunoglobulin or an immunoglobulin fragment Ig' and V is a vinca moiety I where $R^7$ is an open bond. The immunoglobulin, or fragment, can be modified by coupling with 1–20, preferably 2–10, of the vinca residues shown. Immunoglobulins specific to antigens on the surface of cells to be killed, and techniques for their production from the serum of immunized animals or by culturing hybridomas secreting monoclonal products, are well known. The preferred type of antibody for use in the invention is an immunoglobulin of the IgG or IgM class. Some representative immunoglobulins are as follows, mono- or polyclonal antibodies to (i) human or animal tumour associated antigens
(ii) human B- and T-cell antigens
(iii) human Ia antigens
(iv) viral, fungal and bacterial antigens
(v) cells involved in human inflammatory or allergic reactions Of the preferred antibodies to human or animal tumour associated antigens there may be mentioned:

(i) Ig from goats or sheep immunised with carcinoembryonic antigen
(ii) Ig from rabbit antiacute lymphoblastic leukemia serum
(iii) Ig from various primate antisera raised against acute lymphoblastic leukemia, acute myleoblastic leukemia, chronic lymphoblastic leukemia and chronic granulocytic leukemia
(iv) Ig from goats or sheep immunised with lung carcinoma material
(v) monoclonal Ig from mouse hybridomas secreting anti-human colorectal carcinoma antibodies
(vi) monoclonal Ig from mouse hybridomas secreting anti-human melanoma antibodies
(vii) monoclonal Ig from mouse hybridomas secreting reacting with human leukemia cells
(viii) monoclonal Ig from mouse hybridomas secreting antibodies reacting with human neuroblastoma cells (ix) monoclonal Ig from mouse hybridomas secreting antibodies reacting with human breast cancer antigens (x) monoclonal Ig from mouse hybridomas secreting antibodies reacting with human ovarian carcinoma cells (xi) monoclonal Ig from mouse hybridomas secreting antibodies reacting with human osteosarcoma cells (xii) monoclonal Ig from mouse hybridomas secreting antibodies to lung carcinoma.

As indicated above, the conjugate can also be made with immunoglobulin fragments, Ig' collectively, also referred to as Fab, Fab' or F(ab')$_2$ or IgM monomer derived from an antibody by, for example, proteolytic enzyme digestion. Such materials and methods of preparation are well known and it may be mentioned that preferred proteolytic enzymes are pepsin and papain. The Ig'fragment, such as Fab may have to be modified by adding to the poly-peptide chain, one or more amino acid residues so as to confer resistance to continued enzymatic degradation of the Ig' immunoglobulin fragment.

Preferred conjugates of the invention are those derived from 4-succinoylvinblastine 3-carboxhydrazide N$^2$-succinimide and Ig is preferably a monoclonal antibody to a human or animal tumour antigen.

The conjugates of the invention can be prepared by reacting an immunoglobulin or an immunoglobulin fragment with a hemi-acid comprising a vinca moiety having the group OCOXCOOH (R$^8$ is OH) attached at the 4-position. This carboxylic acid is converted to an acylating group, COZ where Z is Cl, Br, N$_3$, imidazolyl,

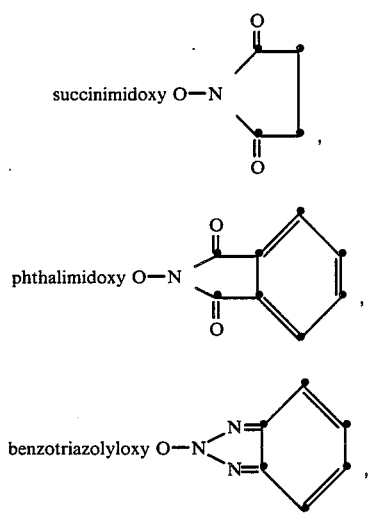

methanesulfonyloxy, tosyloxy, benzenesulfonyloxy or the like acylating group when Z' is imidazolyl, it can be prepared by the use of carbonyl di-imidazole. The intermediate containing the C-4 OCOXCOZ moiety is reacted with the immunoglobulin or immunoglobulin fragment to form the novel conjugates of this invention.

In general, Z is a leaving group which can be any of the well known groups employed in peptide chemistry to establish a covalent amide link (—CONH—) between the conjugating vinca and a free amino group on the immunoglobulin molecule or immunoglobulin fragment. Such groups are well known in the art and a few are illustrated above. Preferred examples are vinca C-4 derivatives VCOXCOZ in which Z is the residue of an N-acylhydroxylamine, for instance, the N-hydroxysuccinimide esters prepared by use of 1-cyclohexyl-3-(2-morpholinoethyl)carbodiimide metho-p-toluenesulphonate or 1,3-dicyclohexyl-carbodiimide, or via a mixed anhydride such as that obtained by using an alkyl chloroformate such as isobutyl chloroformate.

Reaction of an immunoglobulin or immunoglobulin fragment with a 3-carboxhydrazide N$^2$-succinimide, adipimide or glutarimide derivative of a vinca containing a COXCOZ a group at C-4 is preferably carried out in aqueous media at a temperature of from 5° C. to 25° C., for example at room temperature, and at a pH of 7.5 to 9.5, preferably 8.0 9.0. The process results in the attachment by covalent linkage of one or more vinca residues at a free amino or free hydroxy or free thiol group of the immunoglobulin molecule, for example, on the amino groups of a lysine residues. The number of residues attached will depend on the concentration of the reactants and the duration of the reaction but the average number is usually for example from 1 or 3 to 14 or 20.

For example, in carrying out the reaction, a solution of the compound of formula I where R$^7$ is COXCOR$^8$ and R$^8$ is Z in a suitable solvent such as dimethylformamide is slowly added dropwise to a buffered solution of immunoglobulin in for example 0.34M borate buffer at pH 8.6. The conjugate is isolated by gel filtration and stored in saturated ammonium sulphate solution being readily brought back into solution by dialysis with a buffer solution for example a phosphate buffered saline pH 7.4, or alternatively it can be stored in a refrigerator at 4° C. or frozen at for example $-20°$ C.

Evaluation of the conjugate can be carried out using well known techniques such as affinity chromatography. The efficacy of the conjugate can be estimated by counting the number of viable cells after treatment of a suspension of tumour cells with the conjugate, or from measurements of the uptake of tritiated uridine. Protein and drug concentrations are determined by measuring optical densities of conjugate solutions at two wavelengths, for example 270 and 280 nm, and relating the values obtained to those for the free drug and unconjugated immunoglobulin at the same two wavelengths.

The novel conjugates of the invention are useful in the treatment of cancers and as such are preferably prepared for use in formulations suitable for injection. Thus the invention includes a pharmaceutical formulation, for example an injectable preparation comprising a conjugate of the invention together with a pharmaceutically-acceptable carrier or diluent such as are well known in the art. It is formulated preferably in unit dosage form, each dosage unit containing, for example, from 0.01 to 2 mg of the active ingredient (in terms of the vinca drug moiety).

The novel conjugates are effective over a wide dosage range and for example for the treatment of adult humans suffering from cancer dosages per week will normally fall within the range of 1 to 10 mg/kg (vinca drug moiety), more usually in the range of from 3 to 9 mg/kg. However it will be understood that the amount of compound actually administered will be determined by a physician in the light of the relevant circumstances, including the condition to be treated and the chosen route of administration.

We claim:

1. A compound of the formula:

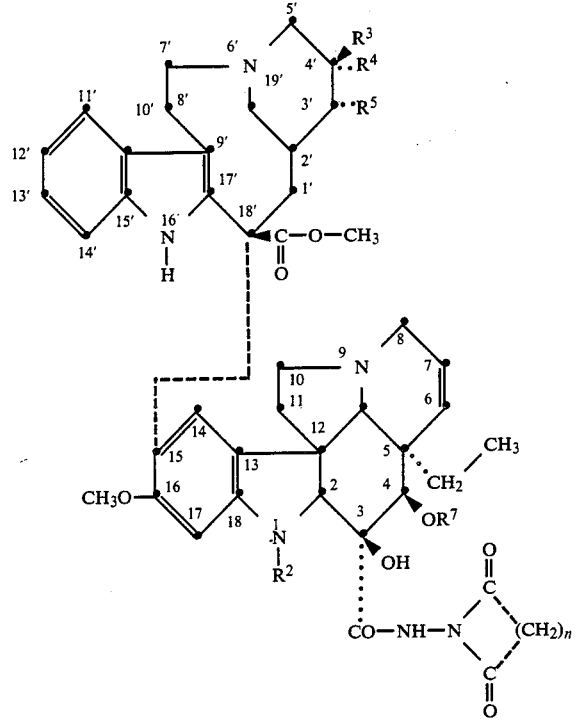

wherein n is 2-4, $R^2$ is $CH_3$ or CHO; when taken singly, $R^5$ is H, and one of $R^3$ and $R^4$ is ethyl and the other is H or OH; when taken together with the carbons to which they are attached, $R^4$ and $R^5$ form an oxirane ring and $R^3$ is ethyl; and $R^7$ is H, $C_{1-3}$ alkyl-CO, chloro-substituted $C_{1-3}$ alkyl-CO, or CO—X—$COR^8$ where $R^8$ is OH, O—$C_{1-3}$ alkyl or Z, X is $C_{2-4}$ alkylene and Z is selected from the group consisting of chloro, bromo, azido, O—CO—$C_{1-6}$ alkyl, imidazolyl, succinimidoxy, phthalimidoxy, and benzotriazolyloxy; and pharmaceutically acceptable acid addition salts thereof.

2. A compound of the formula

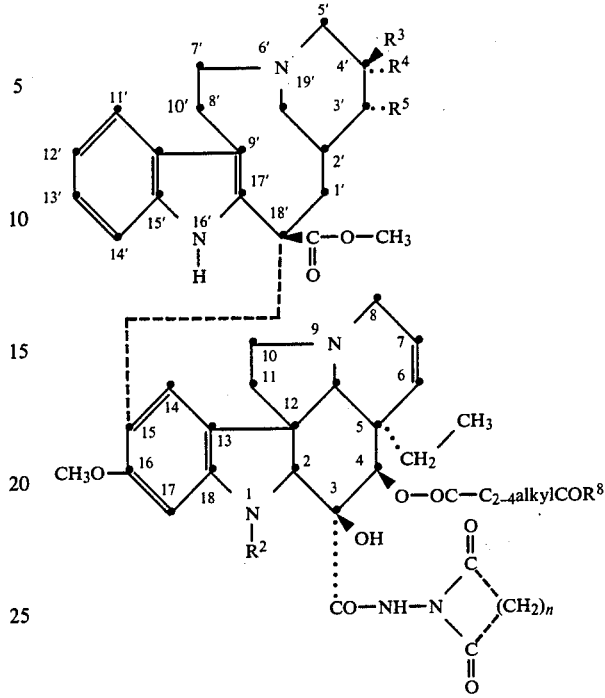

wherein n is 2-4, $R^2$ is H, $CH_3$ or CHO; when taken singly, $R^5$ is H, one of $R^3$ and $R^4$ is ethyl and the other is H or OH; when taken together with the carbons to which they are attached, $R^4$ and $R^5$ form an oxirane ring and $R^3$ is ethyl, and $R^8$ is chloro, bromo, azido, O—CO—$C_{1-6}$ alkyl, imidazolyl, succinimidoxy, phthalimidoxy, benzotriazolyloxy, OH or O—$C_{1-3}$ alkyl.

3. A compound according to claim 1 in which $R^7$ is H.

4. A compound according to claim 1 in which $R^7$ is $C_{1-3}$ alkanoyl or chloroacetyl.

5. A compound according to claim 3, said compound being 4-desacetyl VLB 3-carboxhydrazide $N^2$-succinimide.

6. A compound according to claim 4, said compound being VLB 3-carboxhydrazide $N^2$-succinimide.

7. A compound according to claim 4, said compound being 4-propionyl VLB 3-carboxhydrazide $N^2$-succinimide.

8. A compound according to claim 4, said compound being 4'-deoxy-4-desacetylleurosidine 3-carboxhydrazide $N^2$-succinimide.

9. A compound according to claim 1, said compound being 4-succinoyl VLB 3-carboxhydrazide $N^2$-succinimide.

* * * * *